(12) United States Patent
McNamara

(10) Patent No.: US 10,379,012 B2
(45) Date of Patent: Aug. 13, 2019

(54) SYSTEM FOR CONVERTING PROPELLING THRUST TO PRODUCE A CONTINUOUS FLOW

(71) Applicant: Richard John McNamara, Tampa, FL (US)

(72) Inventor: Richard John McNamara, Tampa, FL (US)

( * ) Notice: Subject to any disclaimer, the term of this patent is extended or adjusted under 35 U.S.C. 154(b) by 0 days.

(21) Appl. No.: 16/248,580

(22) Filed: Jan. 15, 2019

(65) Prior Publication Data

US 2019/0219488 A1   Jul. 18, 2019

Related U.S. Application Data

(60) Provisional application No. 62/618,355, filed on Jan. 17, 2018.

(51) Int. Cl.
*G01N 1/22* (2006.01)
*B64D 47/00* (2006.01)
*B64C 39/02* (2006.01)

(52) U.S. Cl.
CPC ......... *G01N 1/2247* (2013.01); *B64C 39/024* (2013.01); *B64D 47/00* (2013.01); *G01N 1/2273* (2013.01); *B64C 2201/125* (2013.01)

(58) Field of Classification Search
CPC ............ B64C 2230/20; B64C 2230/06; B64C 2201/125; G01N 2201/2279; G01N 2001/2288; G01N 1/24
USPC ............................ 73/863.51, 863.52, 863.53
See application file for complete search history.

(56) References Cited

U.S. PATENT DOCUMENTS

| | | | | |
|---|---|---|---|---|
| 4,571,996 A * | 2/1986 | Wakeman | ............... | G01F 1/684 73/202.5 |
| 5,048,327 A * | 9/1991 | Atwood | .................... | G01F 5/00 73/114.33 |
| 5,627,328 A * | 5/1997 | Sheridan | .............. | G01N 1/2258 73/863.83 |
| 6,192,767 B1 * | 2/2001 | Fiorina | ................ | G01N 1/2273 73/863.21 |
| 6,809,648 B1 | 10/2004 | Ucar | | |
| 7,156,552 B2 | 1/2007 | Ucar | | |
| 7,174,782 B2 * | 2/2007 | Ice | ......................... | G01K 13/02 374/135 |
| 7,998,731 B2 * | 8/2011 | Daitch | ................. | G01N 1/2273 435/287.4 |

(Continued)

*Primary Examiner* — Harshad R Patel
*Assistant Examiner* — Tran M. Tran

(57) ABSTRACT

A system for converting propelling thrust to produce a continuous flow is provided. The system can be integrated and/or retrofitted to the body of an aircraft. The system includes a pressure-lowering device and a sample chamber. The pressure-lowering device is used produce a low-pressure, continuous flow from a high-velocity propelling thrust source. Moreover, the pressure-lowering device is a passive flow generator that does not require a power source in order to produce a continuous flow from a propelling thrust. The design of the pressure-lowering device produces a flow rate that is independent of the aircraft motion. The sample chamber is used to measure and analyze ambient gases which are pulled through the sample chamber by the pressure-lowering device, as a result of the high-velocity air stream produced by the propelling thrust source.

19 Claims, 9 Drawing Sheets

(56) References Cited

U.S. PATENT DOCUMENTS

| | | | | |
|---|---|---|---|---|
| 8,146,445 | B2* | 4/2012 | Ferri | G01N 1/2205 |
| | | | | 73/863.23 |
| 8,539,840 | B2* | 9/2013 | Ariessohn | B08B 3/12 |
| | | | | 73/860 |
| 8,820,672 | B2* | 9/2014 | Erben | B64C 39/024 |
| | | | | 244/1 R |
| 10,094,771 | B2* | 10/2018 | Fetzner | G01N 21/3504 |
| 10,175,151 | B2* | 1/2019 | Avakov | G01N 1/2273 |

* cited by examiner

SYSTEM FOR CONVERTING PROPELLING THRUST TO PRODUCE A CONTINUOUS FLOW

The current application claims a priority to the U.S. Provisional Patent application Ser. No. 62/618,355 filed on Jan. 17, 2018.

FIELD OF THE INVENTION

The present invention relates generally to aircraft measurement tools and assemblies. More specifically, the present invention is a system for converting propelling thrust to produce a continuous flow. The present invention includes a passive flow generator which produces a steady flow for measuring gas samples.

BACKGROUND OF THE INVENTION

Measuring tools have been commonly utilized in aircraft to measure various variables such as air flow speed, pressure, static conditions, etc. Many of these devices are generally installed around the outer surface of an aircraft where these devices are exposed to the elements to be measured. Most of these devices are electrically connected to a computer or control board where the electronic signals generated by the sensors on these devices are read and stored. While these devices have been generally efficient to generate reliable measurements, many of the current available devices have too many limitations which lower the range of applications for these devices. Most of the currently available devices require to be placed and oriented with the main gas flow in order to reliably measure the different variables. For example, devices like pitot-static systems require to be oriented with the air flow in order to properly obtain accurate readings. Other systems such as passive flow systems try to reduce the need of these devices to be properly placed and oriented in order to obtain accurate and reliable measurements. These passive flow systems comprise structures which do not require to be in the orientation of the flow. Instead, these devices rely on passive flow which is generated from the main flow or generated by another mechanism part of the system or aircraft. Unfortunately, most of these systems often require large amounts of power to generate the necessary passive flow in order to obtain accurate measurements. Similarly, passive flow systems which rely on the flow generated by the thrust can only work with high-speed aircraft. Thus, a system, for converting propelling thrust to produce a continuous flow, which can be used to generate constant measuring samples without the need of orientation with the main flow nor the need of a high-speed thrust source to generate a steady air flow, is beneficial and necessary.

An objective of the present invention is to provide a passive flow generator which produces a steady and repeatable flow rate of a gas sample through a sensor or sample chamber for measurement. Another objective of the present invention is to provide a passive flow generator which is low-profile, light-weight, and can be integrated in the body of an aircraft or retrofitted to the body of an aircraft. Additional advantages of the present invention are set forth in part in the description which follows, and in part will be obvious from the description, or may be learned by practice of the invention. Additional advantages of the invention may be realized and attained by means of the instrumentalities and combinations particularly pointed out in the detailed description of the invention section. Further benefits and advantages of the embodiments of the present invention are apparent from consideration of the following detailed description given with reference to the accompanying drawings, which specify and show preferred embodiments of the present invention.

SUMMARY OF THE INVENTION

The present invention is a system for converting a propelling thrust to produce a continuous flow. The present invention is a low-profile, light-weight, non-powered system used to move atmospheric and other airborne gas samples through an in-situ measurement system, without the added weight, bulk and power requirements of other electric vacuum pump systems or relying on significant forward motion of an aircraft platform to produce a constant flow through the sampling system. The present invention is preferably suited for multi-copter and fixed-wing Unmanned Aerial Systems (UAS) where power, size and weight are limited. Potential applications include, but are not limited to: the petrochemical industry, pipeline gas leak detection, atmospheric measurements and research, environmental measurements, agriculture, mining applications, as well as other businesses requiring an accurate and repeatable sample flow generating device. Slow moving, multidirectional/hovering aircraft do not generate the forward velocity required by forward mounted flow-based devices/systems to generate sampling flow rates through sample chambers and across sensors. Multidirectional and hovering vehicles such as UAS multi-copters do not always fly in a forward direction which make forward-facing probes or sample inlets useless anytime the aircraft is hovering or not flying in the direction that points the inlet into the high-velocity air stream generated by the aircraft's forward movement. Slow moving aircraft such as a fixed-wing UAS often do not travel at high speeds and would be incapable of producing the required forward motion to produce an airstream with sufficient velocity for the forward-facing devices to function.

The present invention does not require high speeds or forward movement to produce a predictable, steady flow rate regardless of the aircraft/vehicle orientation or speed. The present invention is located at the end of the sampling process, not at the front as with the forced air systems. Gas samples are drawn into the system by the low pressure generated by the passive flow generator. Low pressure is generated whenever the vehicle's propeller is turning, independent of vehicle motion or orientation. Compression heating from air being forced into the device inlet does not occur in the present invention. Inlet heating due to drag of the sampling probe house found on forward facing devices is also not present or negligible, in the case of a fixed wing UAS flying at relatively slow speeds. The inlet for the present invention can be located anywhere on the vehicle and can even be embedded directly into the vehicle itself as long as the port is free from localized effects of the vehicle. For fixed-wing applications, a static pitot tube can be used to draw the ambient sample. Holes located on the side of the pitot allow the sample to be drawn-in by the passive flow generator without experiencing the effects of a forward-facing inlet probe. This allows samples to be taken free from the localized effects of the aircraft in ambient air. The present invention can be used in applications where an optically based sensor is required. Often optically-based open-path sensors are subject to error from sunlight or other light sources when exposed to the uncontrolled environment found when making in-situ gas measurements. The passive flow generator can be used to draw an ambient sample into an opaque sample chamber where the measurement can be made free from light contamination and still provide a fast-responding measurement.

Response time of various sensors, including some low-cost Microelectromechanical Systems (MEMS) is improved when exposed to a moving gas sample. By introducing a steady flow across a sensor, response time is increased sufficiently to make even some low-cost sensors, suitable for UAS gas measurements. The present invention provides the repeatable steady flow for a better response time to take place without the weight, space, and power requirements associated with a vacuum-pump and without the limitations associated with forward facing forced air systems. The present invention can be designed for a custom specific flow rate or can be used with an inline controller to achieve required flow rate. A UAS equipped with select sensors and the present invention can be utilized to provide reliable ground truth measurements for remote sensing equipment.

DETAIL DESCRIPTIONS OF THE INVENTION

All illustrations of the drawings are for the purpose of describing selected versions of the present invention and are not intended to limit the scope of the present invention.

Figure 6:
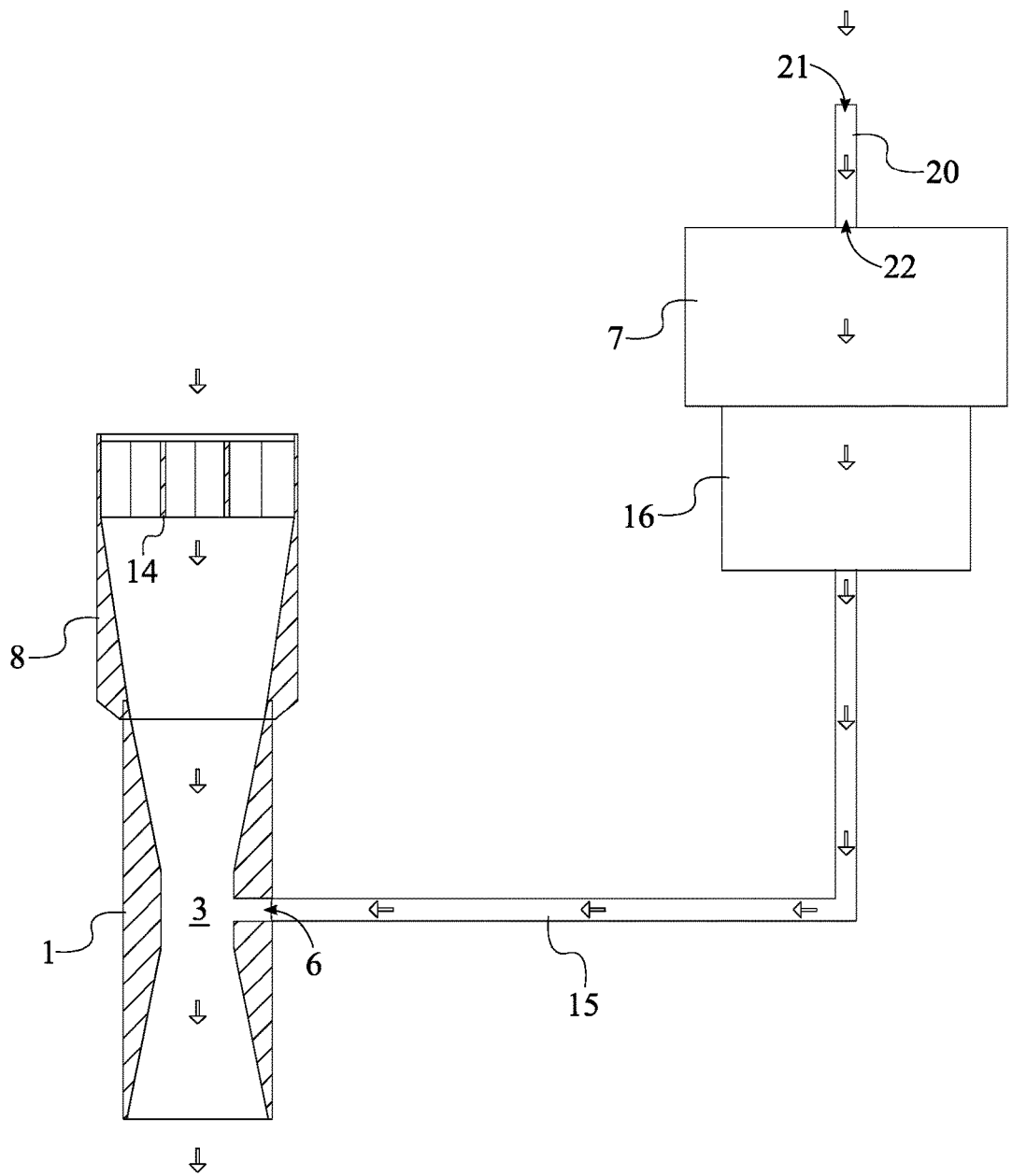
FIG. 6 is a schematic diagram displaying the fluid flow of the present invention.
Figure 7:
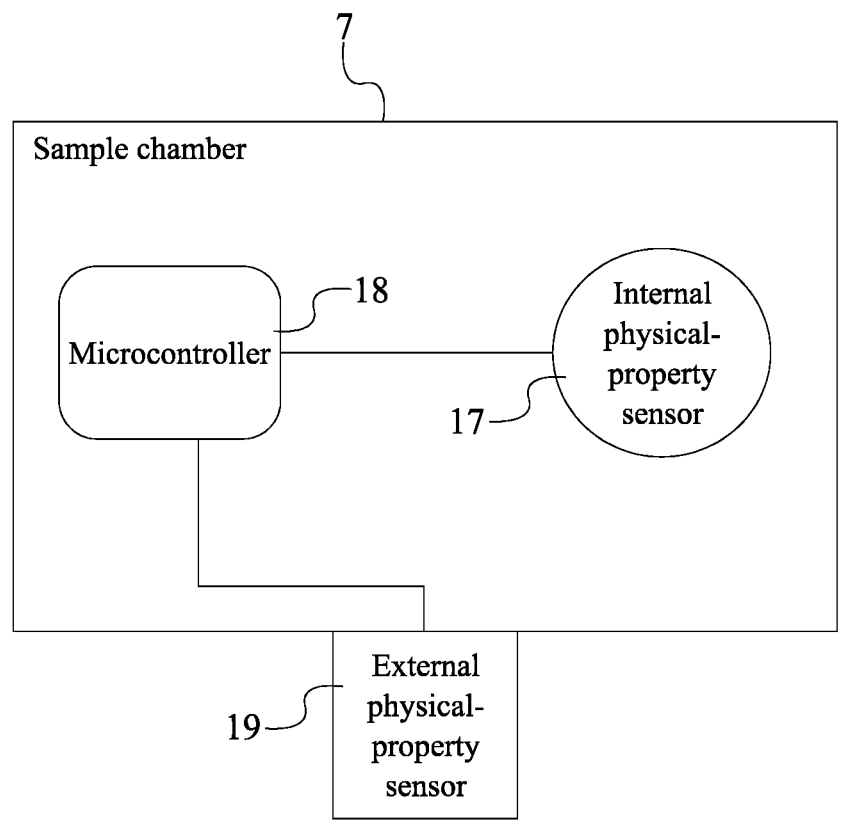
FIG. 7 is a schematic diagram displaying the electronic connections of the present invention.
Figure 8:
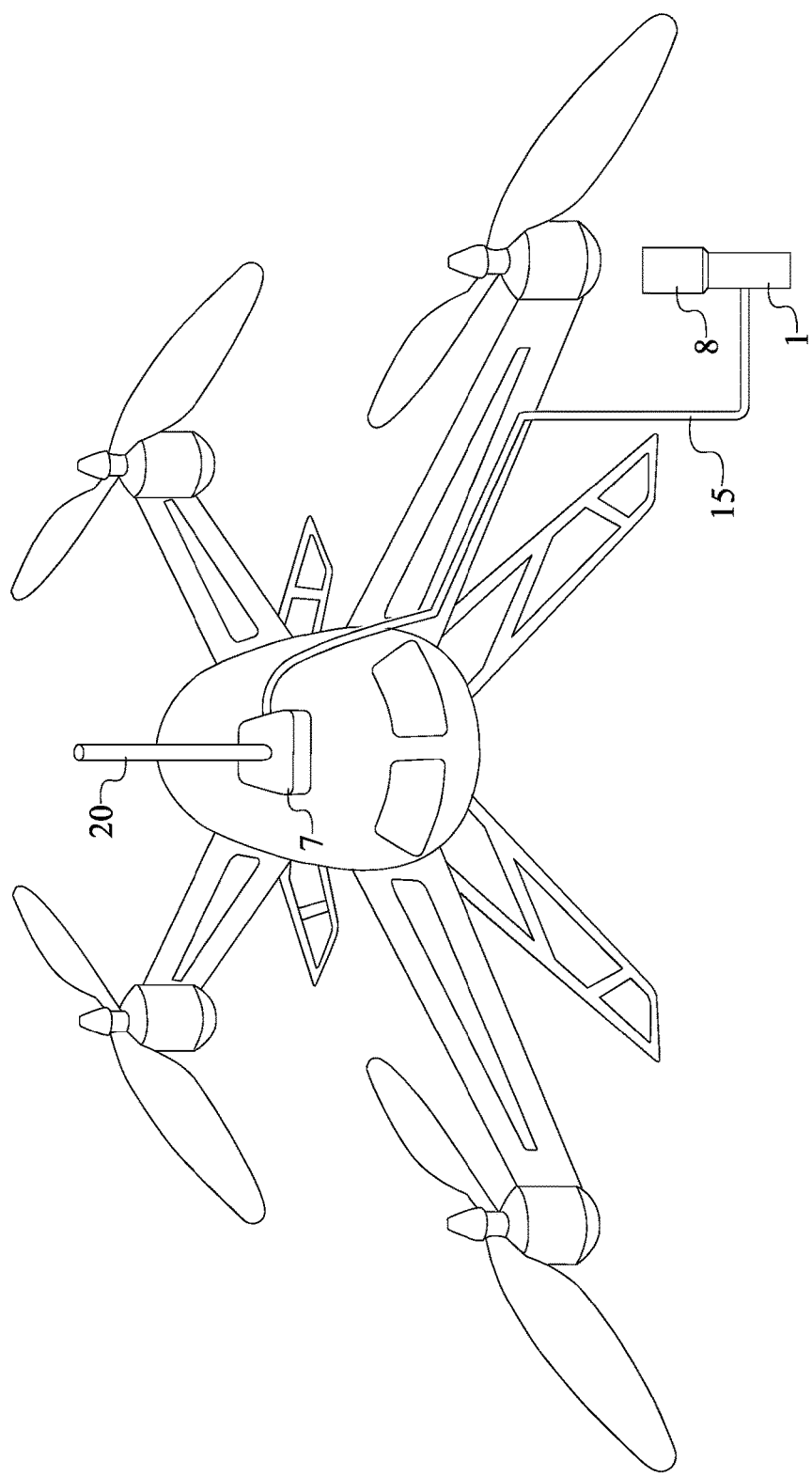
FIG. 8 is a schematic diagram of the present invention displaying the present invention working with an aircraft.
Figure 9:
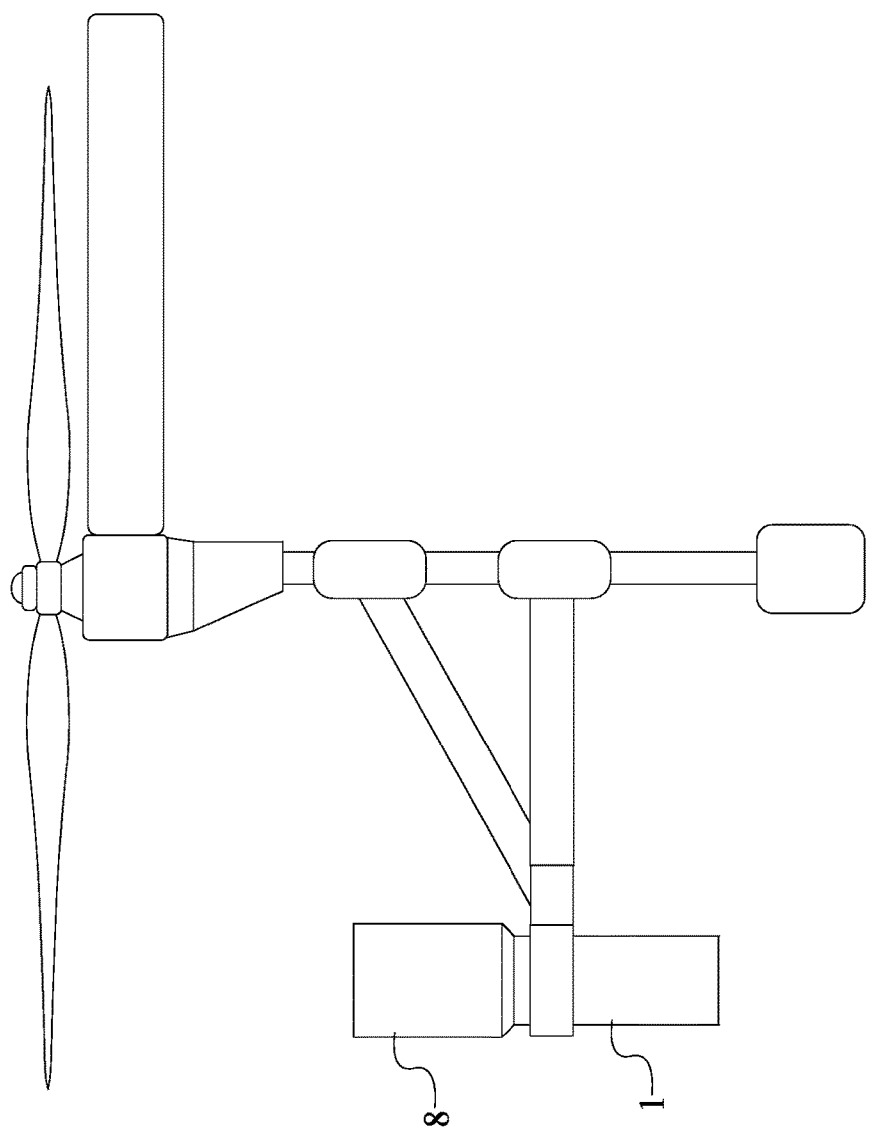
FIG. 9 is a schematic diagram of the present invention displaying the present invention mounted to an aircraft.

In reference to FIGS. 1 through 9, the present invention is a system for converting propelling thrust to produce a continuous flow. The present invention can be integrated and/or retrofitted to the body of an aircraft. The present invention comprises a pressure-lowering device 1 and a sample chamber 7. The pressure-lowering device 1 is used to produce a low-pressure, continuous flow from a high-velocity propelling thrust source. Moreover, the pressure-lowering device 1 is a passive flow generator that does not require a power source in order to produce a continuous flow from a propelling thrust. The propelling thrust source is preferably the high-velocity air stream from the propellers of an aerial vehicle. With reference to FIGS. 8 and 9, the pressure-lowering device 1 is preferably mounted adjacent to the propellers of an aerial vehicle. The geometric parameters of the pressure-lowering device 1 can be varied for generating desired flows specific to an aircraft type, aircraft mounting location, project operating environment, and sensor requirements. The design of the pressure-lowering device 1 produces a flow rate that is independent of the aircraft motion. The sample chamber 7 is used to measure and analyze ambient gases which are pulled through the sample chamber by the pressure-lowering device 1, as a result of the high-velocity air stream produced by the propelling thrust source.

Figure 1:
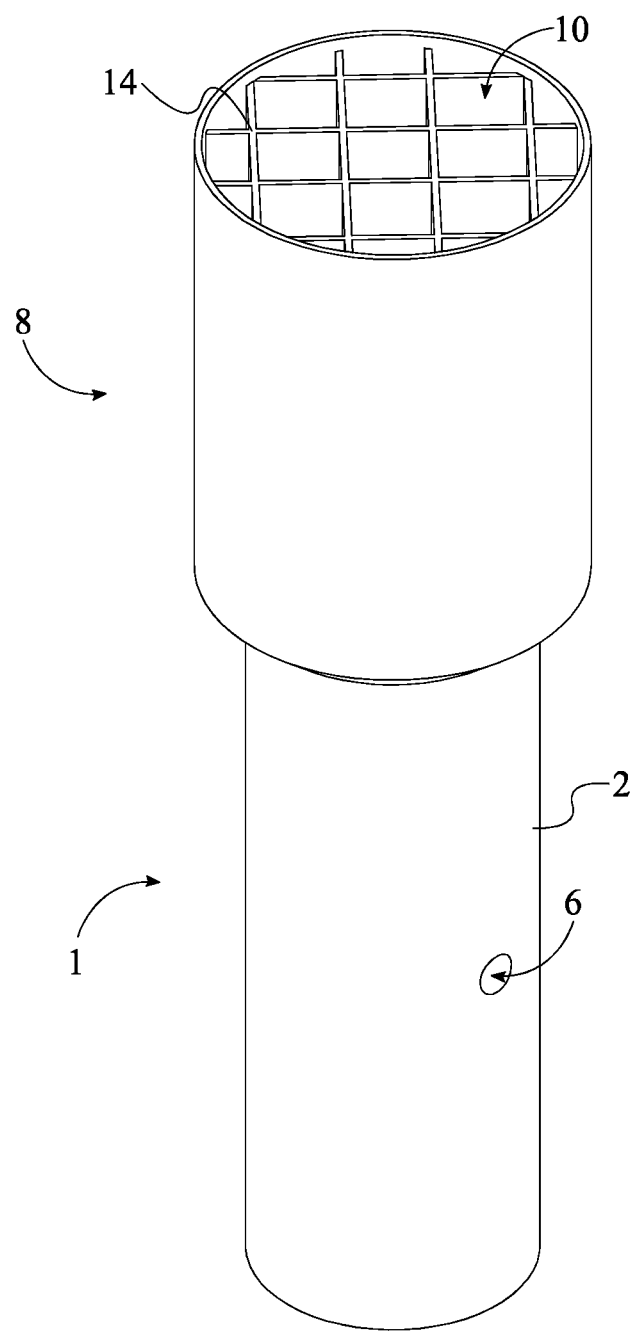
FIG. 1 is a front perspective view of the present invention.
Figure 2:
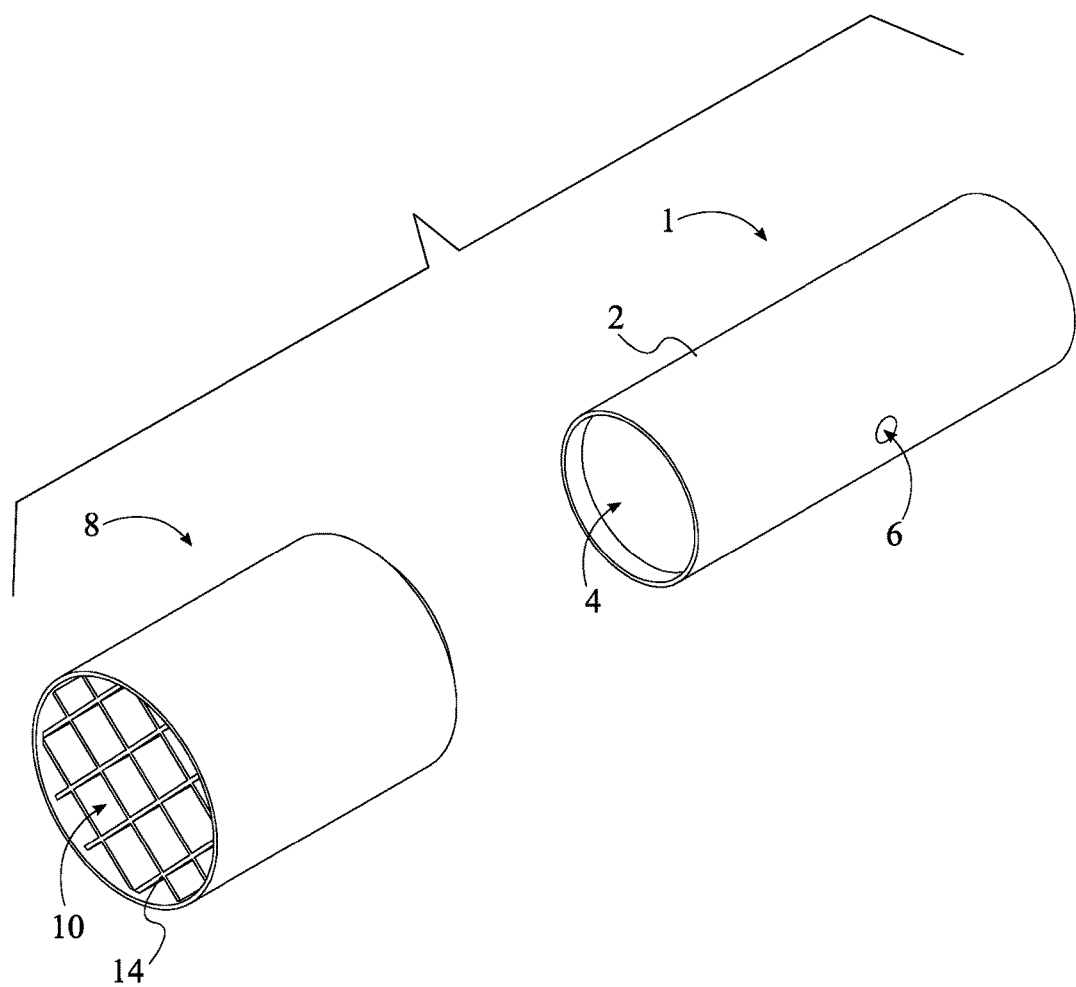
FIG. 2 is a top exploded perspective view of the present invention.
Figure 3:
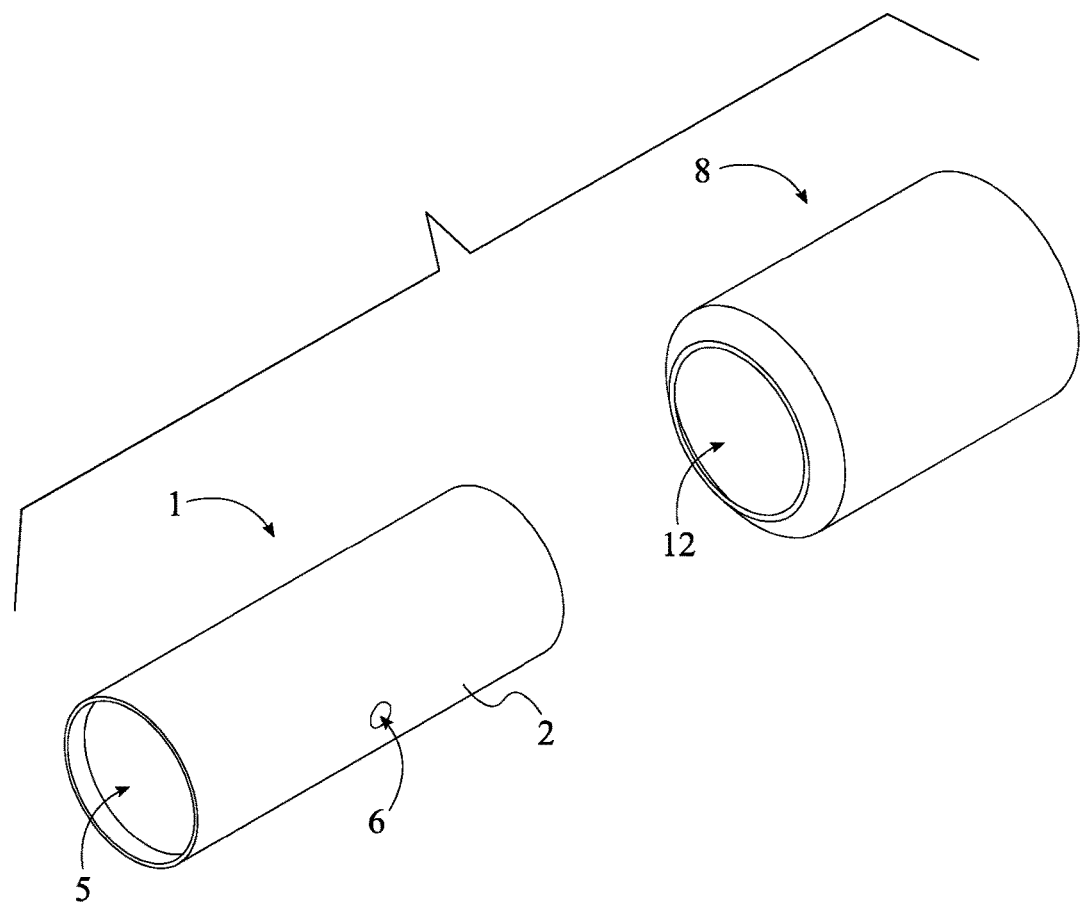
FIG. 3 is a bottom exploded perspective view of the present invention.
Figure 4:
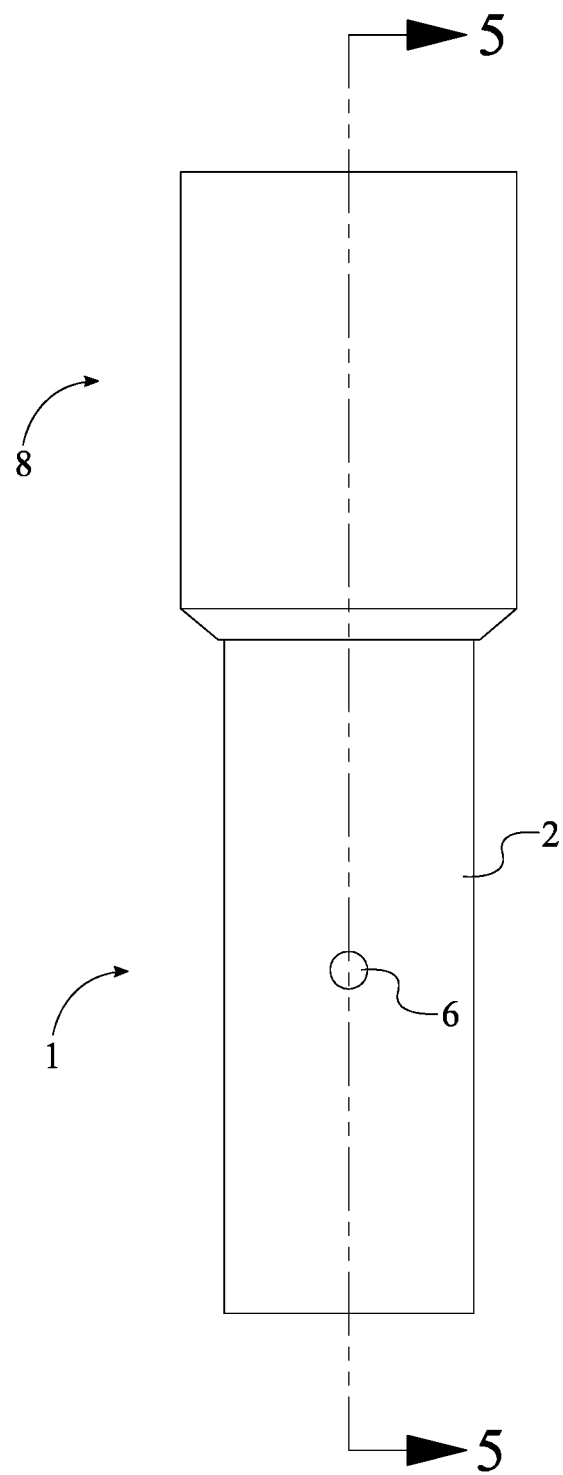
FIG. 4 is a right-side view of the present invention.
Figure 5:
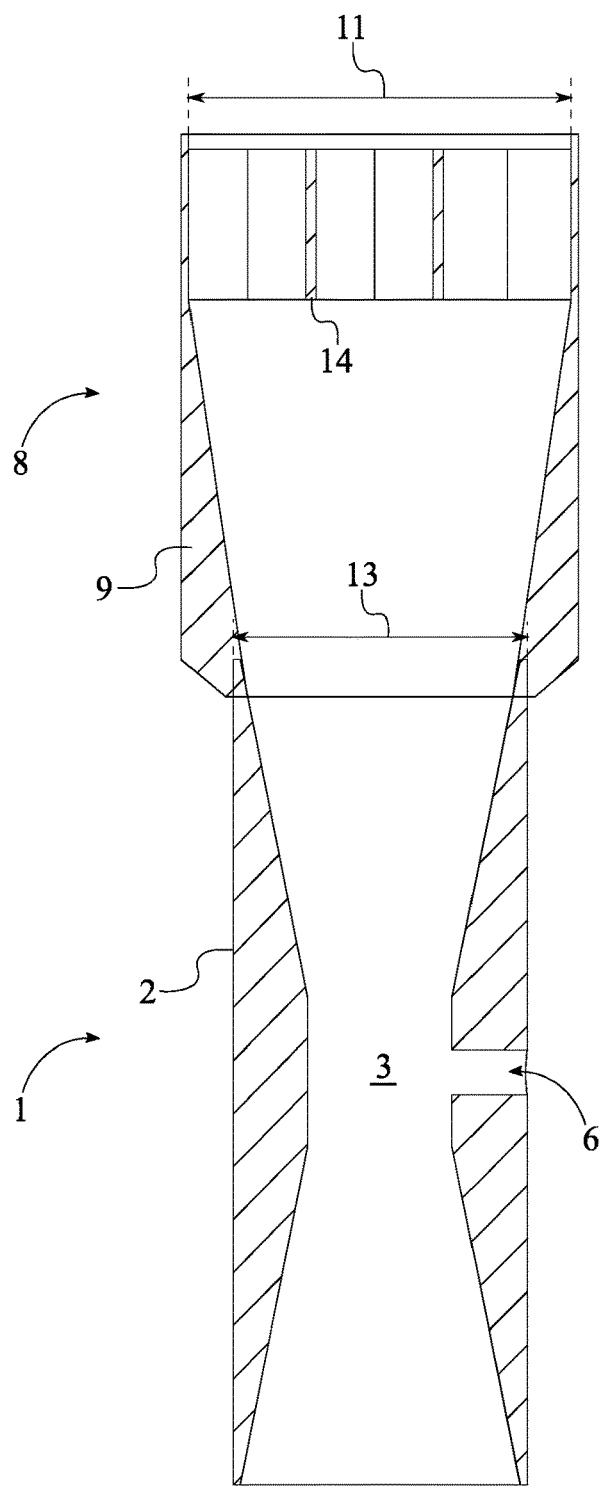
FIG. 5 is a cross-section view taken along line 5-5 in FIG. 4.

The general configuration of the aforementioned components allows the present invention to effectively convert a propelling thrust to produce a continuous flow. With reference to FIGS. 2, 3, and 5, the pressure-lowering device 1 comprises a tubular body 2 and a pressure well 3. The tubular body 2 is the structural form of the pressure-lowering device 1. The pressure well 3 is a designed venturi structure that, through the Bernoulli principle, creates a low-pressure source. The tubular body 2 comprises an inlet open end 4 and an outlet open end 5. The inlet open end 4 and the outlet open end 5 distinguish the ends of the tubular body 2. The inlet open end 4 is positioned collinear with the direction of the air stream generated by the propelling thrust source. The pressure well 3 is connected within the tubular body 2. The pressure well 3 decreases in diameter from each the inlet open end 4 and the outlet open end 5 to the center of the tubular body 2. The inlet open end 4 and the outlet open end 5 are in fluid communication with each other through the pressure well 3. This allows a fluid, a gas, to freely flow through the pressure-lowering device 1. Moreover, this allows the high-velocity stream, produced by the propelling thrust, to freely flow through the pressure-lowering device 1 in order to create a low-pressure source. The pressure-lowering device 1 is externally mounted to the sample chamber 7. This arrangement prevents the high-velocity propelling thrust source from disturbing the measurements taken by the sample chamber 7. The pressure well 3 and the sample chamber 7 are in fluid communication with each other. This allows ambient gases to be pulled through the sample chamber 7 and into the pressure-lowering device 1, as a result of the low-pressure source of the pressure well 3.

In order to improve the airflow through the pressure-lowering device 1 and with reference to FIGS. 2 and 3, the present invention may further comprise an air scoop 8. The air scoop 8 is structurally designed to increase the volume of gas pushed through the pressure-lowering device 1 and to make the pressure-lowering device 1 less sensitive to changes in the velocity of the propelling thrust and the mounting location on an aircraft. The air scoop 8 comprises a scoop inlet 10 and a scoop outlet 12. The scoop inlet 10 and the scoop outlet 12 distinguish ends of the air scoop 8. In order for the propelling thrust to flow from the air scoop 8 to the pressure-lowering device 1, the scoop outlet 12 is hermetically connected to the inlet open end 4.

In order to streamline the turbulent air stream and with reference to FIG. 5, generated by the propeller of an aircraft through the air scoop 8, the present invention may further comprise a baffle 14. Additionally, the baffle 14 provides a more laminar flow inside the pressure-lowering device 1. The air scoop 8 further comprises a tapered portion 9. The tapered portion 9 allows the air scoop 8 to properly provide an adequate flow through the pressure-lowering device 1. The tapered portion 9 includes tapered walls at an angle so as to continue the angle of the inlet open end 4. This reduces turbulence at the scoop inlet 10 and increases air flow through the device. The baffle 14 is mounted within the scoop inlet 10. This arrangement properly positions the baffle 14 within the air scoop 8. The scoop inlet 10 and the scoop outlet 12 are in fluid communication with each other through the tapered portion 9. This allows the air stream of the propelling thrust to be streamlined when passing through the air scoop 8. Furthermore, a diameter 11 of the scoop inlet 10 is preferably larger than a diameter 13 of the scoop outlet 12. This allows air stream of the propelling thrust to efficiently pass through the air scoop 8 and into the pressure-lowering device 1.

With reference to FIGS. 6 and 8, the present invention may further comprise a low-pressure tube 15. The low-pressure tube 15 is the conduit for the fluid communication between the pressure-lowering device 1 and the sample chamber 7. The pressure-lowering device 1 further comprises a low-pressure inlet 6. The low-pressure inlet 6 is used to access the low-pressure source produced by the pressure well 3. The low-pressure inlet 6 laterally traverses into the tubular body 2 and into the pressure well 3. This arrangement allows the low-pressure source of the pressure well 3 to be accessed through the low-pressure inlet 6. Furthermore, the low-pressure inlet 6 and the sample chamber 7 are in fluid communication with each other through the low-pressure tube 15. This arrangement allows the low-pressure source of the pressure well 3 to pull ambient gases through the sample chamber 7 and into the pressure-lowering device 1.

With reference to FIG. 6, the present invention may further comprise a flow-controlling valve 16. The flow-controlling valve 16 is used to regulate the airflow being transferred from the sample chamber 7 and into the pressure-lowering device 1. In order to regulate the air flow from the sample chamber 7 to the pressure-lowering device 1, the pressure well 3 and the sample chamber 7 are in fluid communication with each other through the flow-controlling valve 16.

With reference to FIG. 7, the present invention may further comprise at least one internal physical-property sensor 17 and a microcontroller 18. The at least one internal physical-property sensor 17 may be any sensor such as, but is not limited to, a flow rate sensor and/or a pressure differential sensor. Additionally, the internal physical-property sensor 17 is used to measure and analyze the airflow passing through the sample chamber 7 and to the pressure-lowering device 1. The microcontroller 18 is used to process and manage measurement readings from the internal physical-property sensor 17. The internal physical-property sensor 17 is mounted within the sample chamber 7 in order to measure and analyze the airflow passing through sample chamber 7 and to the pressure-lowering device 1. The microcontroller 18 is electronically connected to the internal physical-property sensor 17 in order to manage the internal physical-property sensor 17.

In another embodiment of the present invention and with reference to FIG. 7, the present invention may further comprise at least one external physical-property sensor 19. The at least one external physical-property sensor 19 may be any sensor such as, but is not limited to, a flow rate sensor and/or pressure differential sensor. Additionally, the external physical-property sensor 19 is used measure and analyze the airflow passing through the sample chamber 7 and to the pressure-lowering device 1. In order to properly measure the airflow passing through the sample chamber 1, the sample chamber 7 and the pressure well 3 are in fluid communication with each other through the external physical-property sensor 19. The microcontroller 18 is used to process and manage measurement readings from the external physical-property sensor 19. In order to manage the external physical property sensor, the microcontroller 18 is electronically connected to the external physical-property sensor 19.

With reference to FIGS. 6 and 8, the present invention may further comprise an ambient-air sampling tube 20. The ambient-air sampling tube 20 is used to collect ambient air and transfer said ambient air into the sample chamber 7. The ambient-air sampling tube 20 comprises an inlet tube end 21 and an outlet tube end 22. The inlet tube end 21 and the outlet tube end 22 distinguish the ends of the ambient-air sampling tube 20. The inlet tube end 21 is positioned offset from the sample chamber 7, and the outlet tube end is in fluid communication with the sample chamber 7. This arrangement allows the ambient-air sampling tube 20 to properly transfer ambient air into the sample chamber 7 and allows the inlet tube end 21 to collect ambient air that is not affected by the turbulence of the high-velocity propelling thrust source.

Although the invention has been explained in relation to its preferred embodiment, it is to be understood that many other possible modifications and variations can be made without departing from the spirit and scope of the invention as hereinafter claimed.

What is claimed is:

1. A system for transferring propelling thrust to produce a continuous flow comprising:
   a pressure-lowering device;
   a sample chamber;
   the pressure-lowering device comprising a tubular body;
   the tubular body comprising a pressure well, an inlet open end and an outlet open end,
   the inlet open end and the outlet open end being in fluid communication with each other through the pressure well;
   the pressure-lowering device being externally mounted to the sample chamber;
   the sample chamber being positioned offset from the inlet open end;
   the pressure well and the sample chamber being in fluid communication with each other;
   an air scoop;
   the air scoop comprising a scoop inlet and a scoop outlet; and
   the scoop outlet being hermetically connected to the inlet open end.

2. The system for transferring propelling thrust to produce a continuous flow as claimed in claim 1 comprising:
   a baffle;
   the air scoop further comprising a tapered portion;
   the baffle being mounted within the scoop inlet; and
   the scoop inlet and the scoop outlet being in fluid communication with each other through the tapered portion.

3. The system for transferring propelling thrust to produce a continuous flow as claimed in claim 1, wherein a diameter of the scoop inlet is larger than a diameter of the scoop outlet.

4. The system for transferring propelling thrust to produce a continuous flow as claimed in claim 1 comprising:
   a low-pressure tube;
   the pressure-lowering device further comprises a low-pressure inlet;
   the low-pressure inlet laterally traversing into the tubular body and into the pressure well; and
   the low-pressure inlet and the sampling chamber being in fluid communication with each other through the low-pressure tube.

5. The system for transferring propelling thrust to produce a continuous flow as claimed in claim 1 comprising:
   a flow controlling valve; and
   the pressure well and the sample chamber being in fluid communication with each other through the flow controlling valve.

6. The system for transferring propelling thrust to produce a continuous flow as claimed in claim 1 comprising:

at least one internal physical-property sensor;
a microcontroller;
the at least one internal physical-property sensor being mounted within the sample chamber; and
the microcontroller being electronically connected to the at least one internal physical-property sensor.

7. The system for transferring propelling thrust to produce a continuous flow as claimed in claim 1 comprising:
at least one external physical-property sensor;
a microcontroller;
the pressure well and the sample chamber being in fluid communication with each other through the at least one external physical-property sensor; and
the microcontroller being electronically connected to the at least one external physical-property sensor.

8. The system for transferring propelling thrust to produce a continuous flow as claimed in claim 1 comprising:
an ambient-air sampling tube;
the ambient-air sampling tube comprising an inlet tube end and an outlet tube end;
the inlet tube end being positioned offset from the sample chamber; and
the outlet tube end being in fluid communication with the sample chamber.

9. A system for transferring propelling thrust to produce a continuous flow comprising:
a pressure-lowering device;
a sample chamber;
an air scoop;
an ambient-air sampling tube;
the pressure-lowering device comprising a tubular body;
the tubular body comprising a pressure well, an inlet open end and an outlet open end,
the inlet open end and the outlet open end being in fluid communication with each other through the pressure well;
the pressure lowering device being externally mounted to the sample chamber; the sample chamber being positioned offset from the inlet open end;
the pressure well and the sample chamber being in fluid communication with each other;
the air scoop comprising a scoop inlet and a scoop outlet;
the scoop outlet being hermetically connected to the inlet open end;
the ambient-air sampling tube comprising an inlet tube end and an outlet tube end;
the inlet tube end being positioned offset from the sample chamber;
the outlet tube end being in fluid communication with the sample chamber.

10. The system for transferring propelling thrust to produce a continuous flow as claimed in claim 9 comprising:
a baffle;
the air scoop further comprising a tapered portion;
the baffle being mounted within the scoop inlet; and
the scoop inlet and the scoop outlet being in fluid communication with each other through the tapered portion.

11. The system for transferring propelling thrust to produce a continuous flow as claimed in claim 9, wherein a diameter of the scoop inlet is larger than a diameter of the scoop outlet.

12. The system for transferring propelling thrust to produce a continuous flow as claimed in claim 9 comprising:
a low-pressure tube;
the pressure-lowering device further comprises a low-pressure inlet;
the low-pressure inlet laterally traversing into the tubular body and into the pressure well; and
the low-pressure inlet and the sampling chamber being in fluid communication with each other through the low-pressure tube.

13. The system for transferring propelling thrust to produce a continuous flow as claimed in claim 9 comprising:
a flow controlling valve; and
the pressure well and the sample chamber being in fluid communication with each other through the flow controlling valve.

14. The system for transferring propelling thrust to produce a continuous flow as claimed in claim 9 comprising:
at least one internal physical-property sensor;
a microcontroller;
the at least one internal physical-property sensor being mounted within the sample chamber; and
the microcontroller being electronically connected to the at least one internal physical-property sensor.

15. The system for transferring propelling thrust to produce a continuous flow as claimed in claim 9 comprising:
at least one external physical-property sensor;
a microcontroller;
the pressure well and the sample chamber being in fluid communication with each other through the at least one external physical-property sensor; and
the microcontroller being electronically connected to the at least one external physical-property sensor.

16. A system for transferring propelling thrust to produce a continuous flow comprising:
a pressure-lowering device;
a sample chamber;
an air scoop;
an ambient-air sampling tube;
a low-pressure tube;
a baffle;
the pressure-lowering device comprising a tubular body;
the tubular body comprising a pressure well, an inlet open end and an outlet open end,
the inlet open end and the outlet open end being in fluid communication with each other through the pressure well;
the pressure-lowering device being externally mounted to the sample chamber;
the sample chamber being positioned offset from the inlet open end;
the pressure well and the sample chamber being in fluid communication with each other;
the air scoop comprising a scoop inlet and a scoop outlet;
the scoop outlet being hermetically connected to the inlet open end;
the ambient-air sampling tube comprising an inlet tube end and an outlet tube end;
the inlet tube end being positioned offset from the sample chamber;
the outlet tube end being in fluid communication with the sample chamber;
the pressure-lowering device further comprising a low-pressure inlet;
the low-pressure inlet laterally traversing into the tubular body and into the pressure well;
the low-pressure inlet and the sampling chamber being in fluid communication with each other through the low-pressure tube;
the air scoop further comprising a tapered portion;
the baffle being mounted within the scoop inlet; and the scoop inlet and the scoop outlet being in fluid communication with each other through the tapered portion.

17. The system for transferring propelling thrust to produce a continuous flow as claimed in claim 16, wherein a diameter of the scoop inlet is larger than a diameter of the scoop outlet.

18. The system for transferring propelling thrust to produce a continuous flow as claimed in claim 16 comprising:
   a flow controlling valve; and
   the pressure well and the sample chamber being in fluid communication with each other through the flow controlling valve.

19. The system for transferring propelling thrust to produce a continuous flow as claimed in claim 16 comprising:
   at least one internal physical-property sensor;
   a microcontroller;
   at least one external physical-property sensor;
   the at least one internal physical-property sensor being mounted within the sample chamber;
   the microcontroller being electronically connected to the at least one internal physical-property sensor;
   the pressure well and the sample chamber being in fluid communication with each other through the at least one external physical-property sensor; and
   the microcontroller being electronically connected to the at least one external physical-property sensor.

* * * * *